United States Patent
Li et al.

(10) Patent No.: US 12,287,283 B2
(45) Date of Patent: Apr. 29, 2025

(54) LINEARIZED OPTICAL SENSOR CALIBRATION FOR MEASURING CALCIUM

(71) Applicant: Ecolab USA Inc., Saint Paul, MN (US)

(72) Inventors: Hui Li, Bolingbrook, IL (US); Bingzhi Chen, Naperville, IL (US); Brandon Davis, Oswego, IL (US)

(73) Assignee: Ecolab USA Inc., Saint Paul, MN (US)

( * ) Notice: Subject to any disclaimer, the term of this patent is extended or adjusted under 35 U.S.C. 154(b) by 602 days.

(21) Appl. No.: 17/363,657

(22) Filed: Jun. 30, 2021

(65) Prior Publication Data
US 2021/0404950 A1  Dec. 30, 2021

Related U.S. Application Data

(60) Provisional application No. 63/046,286, filed on Jun. 30, 2020.

(51) Int. Cl.
*G01N 21/31* (2006.01)
*G01N 33/18* (2006.01)

(52) U.S. Cl.
CPC .......... *G01N 21/31* (2013.01); *G01N 33/1826* (2013.01); *G01N 2201/12746* (2013.01)

(58) Field of Classification Search
CPC .............. G01N 21/31; G01N 33/1826; G01N 2001/2893; G01N 21/274;
(Continued)

(56) References Cited

U.S. PATENT DOCUMENTS 6,360,582 B1  3/2002  Chelvayohan et al.
6,387,709 B1  5/2002  Mason et al.
(Continued)

FOREIGN PATENT DOCUMENTS

EP  3012804 A1  4/2016
EP  3150996 A1  4/2017
(Continued)

OTHER PUBLICATIONS

International Patent Application No. PCT/US2021/039830, International Search Report and Written Opinion mailed Sep. 24, 2021, 13 pages.

*Primary Examiner* — Brian R Gordon
*Assistant Examiner* — Dwan A Gerido
(74) *Attorney, Agent, or Firm* — Fredrikson & Byron, P.A.

(57) ABSTRACT

An optical sensor may be used to measure the concentration of calcium in a water sample, such as a water sample obtained from industrial process water system like a cooling tower system, a boiler water system, or a waste water system. To measure the concentration of calcium, an indicator or reagent may be added to the water sample to form a complex that absorbs light. The absorbance profile of the complex may be non-linear over a range of calcium concentrations. However, the absorbance profile can be linearized to provide calibration coefficients that are subsequently used to determine the concentration of calcium in samples having unknown calcium concentrations. The linearization of the absorbance profile can allow the optical sensor to be calibrated using two solutions. This can reduce the complexity and cost of calibrating the optical sensor, which may otherwise require at least three calibration solutions to capture the non-linear profile of the absorbance curve.

22 Claims, 9 Drawing Sheets

(58) Field of Classification Search
CPC ..... G01N 2201/1288; G01N 2223/303; G01N 2201/12746
See application file for complete search history.

(56) References Cited

U.S. PATENT DOCUMENTS

| | | |
|---|---|---|
| 7,544,516 B2 | 6/2009 | Noda et al. |
| 8,076,154 B2 | 12/2011 | Erickson et al. |
| 10,317,385 B2 | 6/2019 | Li et al. |
| 2007/0084721 A1 | 4/2007 | Hsung et al. |
| 2009/0150106 A1* | 6/2009 | Erickson .............. G01N 21/274 702/85 |
| 2010/0107723 A1 | 5/2010 | Hajishah et al. |
| 2012/0277566 A1 | 11/2012 | Kamath et al. |
| 2015/0198540 A1* | 7/2015 | Zheng .................... G01N 31/22 436/79 |
| 2017/0097300 A1* | 4/2017 | Lu .......................... G01N 21/27 |

FOREIGN PATENT DOCUMENTS

| | | |
|---|---|---|
| JP | 2008058033 A | 3/2008 |
| WO | 2016133882 A1 | 8/2016 |

\* cited by examiner

LINEARIZED OPTICAL SENSOR CALIBRATION FOR MEASURING CALCIUM

RELATED APPLICATIONS

This application claims the benefit of U.S. Provisional Patent Application No. 63/046,286, filed Jun. 30, 2020, the entire contents of which are incorporated herein by reference.

TECHNICAL FIELD

This disclosure relates to optical sensors and, more particularly, to the calibration of optical sensors used to monitor calcium concentrations in industrial water systems.

BACKGROUND

Calcium ions in industrial water systems can cause process inefficiencies and system shutdowns. For example, in cooling water systems, calcium ions present in the recirculating water can lead to calcium-based deposit formation, such as calcium carbonate, calcium phosphate, and/or calcium sulfate scaling. This deposit formation can reduce the heat transfer efficiency and flow capacity of the water system. Preventative steps, such as controlling the operating conditions of the industrial water system and/or adding a control agent to the industrial water may be implemented to prevent or inhibit the formation of calcium-containing deposits.

Optical analysis can be used to measure the concentration of calcium in an industrial water system. However, the accuracy of the analysis is dependent on several factors. For example, operational variables such as flowrate, water pressure, and temperature can change between experimental runs, leading to inconsistent performance of the optical analysis instrument. In addition, the concentration of reagents can vary based on the commercial source, age, and manufacture of the reagent batch. Variation of equipment components such as pumps, LEDs, and system electronics can change over time, impacting the analytical accuracy and reproducibility.

An optical sensor used for optical analysis may be periodically recalibrated to account for changing conditions that can influence the accuracy of measurements made by the sensor. The complexity and amount of operator involvement required to perform the recalibration may depend on the configuration of the optical sensor and the optical response of the material being measured.

SUMMARY

In general, this disclosure is directed to devices, systems, and techniques for calibrating an optical sensor used to measure a concentration of calcium in an industrial water sample and controlling chemical addition based on measurements made by the optical sensor so calibrated. The industrial water sample may be mixed with an indicator that complexes or otherwise reacts with calcium in the water sample, causing a measurable color change proportional to the amount of calcium present in the water sample. The water sample can be optically analyzed by emitting light into the sample and subsequently detecting light from the sample to determine an optical response, such as absorbance, of the sample at one or more wavelengths. The optical response information can be processed with calibration information relating known light absorbance characteristics to known calcium concentrations, thereby providing a measured calcium concentration corresponding to the measured optical response information from the sample.

In practice, the relationship between the optical response of the sample (containing at least calcium and an indicator reagent) and the calcium concentration of the sample may be non-linear. In other words, the optical response of the sample may not increase or decrease linearly with changing calcium concentration but instead may define a curve (e.g., second or higher order polynomial, a power law, an index function curve, a logarithmic curve) providing a more complex relationship between optical response and calcium concentration. This can make recalibration of the optical sensor difficult and expensive, particularly when implemented automatically and/or in the field with more limited resources challenging.

If a sample system exhibits a linear relationship between optical response and calcium concentration, the system may be calibrated using a two-point calibration. For example, the system may be calibrated by measuring the optical response of a first calibration solution having a first known calcium concentration (e.g., which may be a calcium concentration of zero) and a second calibration solution having a second known calcium concentration. Optical response data corresponding to these two known calcium concentrations can be used to define the linear calibration curve for the optical sensor.

By contrast, if the sample system exhibits a non-linear relationship between optical response and calcium concentration, a multi-point calibration utilizing three or more calibration solutions may typically be required to calibrate the system. The use of multiple calibration solutions each with a different calcium concentration may be needed to measure the non-linearity of the calibration curve for calibrating the sensor. This can increase the cost and complexity of the calibration process and/or equipment over a two-point calibration, e.g., by requiring additional calibration solutions and calibration steps to produce a calibration curve that can be used for subsequent sample analysis.

In accordance with some examples of the present disclosure, optical sensor systems and techniques are provided that linearize a non-linear relationship between optical response and calcium concentration and then calibrate the optical sensor using the linearized relationship. Because the calibration relationship between optical response measurements made by the sensor and the calcium concentration in the sample has been linearized, the optical sensor may be calibrated using a two-point calibration instead of a multi-point calibration utilizing three or more calibration points. The optical sensor so calibrated can then be used to measure the optical response of samples having an unknown calcium concentration, thereby providing a measured calcium concentration for the sample based on the measured optical response and the calibration information. This measured calcium concentration information can then be used to control the operating conditions of the industrial water system and/or control addition of a calcium control agent to the industrial water, e.g., that prevents or inhibits the formation of calcium-containing deposits.

In some implementations, an optical sensor for a sample having a calcium-indicator complex that exhibits a non-linear relationship between light absorbance and calcium concentration is calibrated using a two-point calibration. Two calibration solutions having different known concentrations of calcium (e.g., one of which may be devoid of calcium) can be optically analyzed using the sensor to obtain optical response measurements at two wavelengths. An optical response ratio for each calibration solution can be determined by determining a ratio of the optical response measurement made at one wavelength for the calibration solution to the optical response measurement made at the second wavelength for the calibration solution. A calibration data point can be defined for each calibration solution based on this optical response ratio for the calibration solution and the known calcium concentration for the calibration solution. The two calibration data points can define a linear calibration curve that can be stored for subsequent use when making calcium concentration measurements with the optical sensor.

In one example, a method of calibrating an optical sensor for measuring calcium is described. The method involves measuring, with an optical sensor, an absorbance of a first calibration solution at a first wavelength (e.g., first wavelength band) to provide a first measured absorbance for the first calibration solution and at a second wavelength (e.g., second wavelength band) to provide a second measured absorbance for the first calibration solution, the first calibration solution comprising a first known concentration of calcium. The method further involves measuring, with the optical sensor, the absorbance of a second calibration solution at the first wavelength to provide a first measured absorbance for the second calibration solution and at a second wavelength to provide a second measured absorbance, the second calibration solution having a second known concentration of calcium. The method involves determining a first absorbance ratio for the first calibration solution based on the first measured absorbance for the first calibration solution and the second measured absorbance for the first calibration solution and determining a second absorbance ratio for the second calibration solution based on the first measured absorbance for the second calibration solution and the second measured absorbance for the second calibration solution. The method further involves determining coefficients for a linear calibration curve relating an absorbance measurement made by the optical sensor to a calcium concentration in a solution based on the first known concentration of calcium and first absorbance ratio and the second known calcium concentration and the second absorbance ratio and storing the coefficients for the linear calibration curve in a memory associated with the optical sensor.

In another example, a system is described that includes an optical sensor, a calibration solution, a source of an indicator, at least one pump, and a controller. The optical sensor is configured to receive a sample of water containing an unknown concentration of calcium from an industrial water system. The calibration solution has a known concentration of calcium. The at least one pump is fluidly coupled to the source of the indicator and the calibration solution. The controller is communicatively coupled to the optical sensor and the pump. The example specifies that the controller is configured to control the pump to generate a first calibration solution comprising a first known concentration of calcium and the indicator and a second calibration solution having a second known concentration of calcium and the indicator. The controller is further configured to control the optical sensor to measure an absorbance of the first calibration solution at a first wavelength to provide a first measured absorbance for the first calibration solution and at a second wavelength to provide a second measured absorbance for the first calibration solution. In addition, the example specifies that the controller is configured to control the optical sensor to measure the absorbance of the second calibration solution at the first wavelength to provide a first measured absorbance for the second calibration solution and at a second wavelength to provide a second measured absorbance. Also, the controller determines a first absorbance ratio for the first calibration solution based on the first measured absorbance for the first calibration solution and the second measured absorbance for the first calibration solution and determines a second absorbance ratio for the second calibration solution based on the first measured absorbance for the second calibration solution and the second measured absorbance for the second calibration solution. The example specifies that the controller is also configured to determine coefficients for a linear calibration curve relating an absorbance measurement made by the optical sensor to a calcium concentration based on the first known concentration of calcium and first absorbance ratio and the second known calcium concentration and the second absorbance ratio and store the coefficients for the linear calibration curve in a memory associated with the optical sensor.

The details of one or more examples are set forth in the accompanying drawings and the description below. Other features, objects, and advantages will be apparent from the description and drawings, and from the claims.

DETAILED DESCRIPTION

Figure 1:
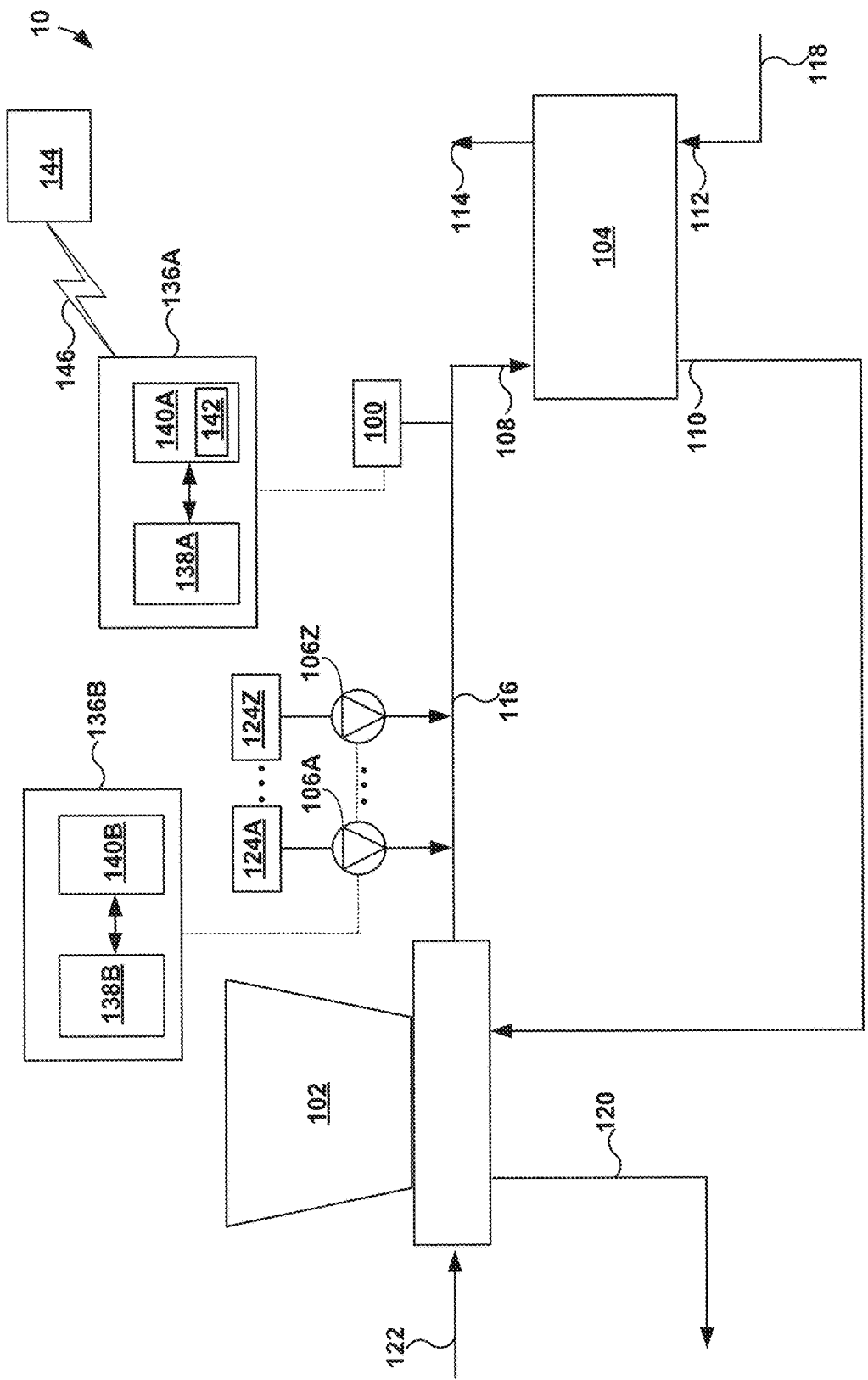
FIG. 1 is a conceptual diagram of an example cooling water system with an example optical sensor according to the disclosure.

This disclosure is generally directed to systems and techniques involving the measurement calcium in water using an optical sensor. A sample of the water may be mixed with an indicator (and optionally other constituent ingredients, such as a pH buffer, range extenders, and the like) that complexes with the calcium in the water to provide a calcium-indicator complex. The calcium-indicator complex can absorb light, with the amount of light absorbed being proportional to the amount of calcium in the sample. This can allow the calcium concentration in the sample to be measured via optical inspection. Various control actions can be taken based on the measured calcium concentration. For example, the operating conditions of the system containing the water may be adjusted (e.g., by changing a temperature and/or flow rate), the makeup of the water may be adjusted (e.g., by partially or fully replacing a recirculating water with freshwater having a lower calcium concentration), and/or one or more chemical agents may be added to the water to control the calcium in the water.

Ensuring that the optical sensor provides an accurate calcium concentration measurement can help ensure that an operator of the system from which the water sample is extracted takes timely and appropriate corresponding control actions. To help ensure that the optical sensor accurately measures the calcium concentration in the water being analyzed, the optical sensor may be calibrated and periodically recalibrated. Recalibration of the optical sensor can address changing internal conditions (e.g., electrical component degradation and sensor drift) and/or changing external conditions (e.g., fouling on an optical window of the sensor) that may impact the accuracy of measurements made using the sensor.

In some implementations according to the present disclosure, an optical sensor for measuring calcium can be calibrated using two-point calibration technique. The two-point calibration technique may involve measuring the optical response of a first calibration solution having a first known calcium concentration and measuring the optical response of a second calibration solution having a second known calcium concentration. This can provide two data points defining a calibration curve (more particularly, a calibration line) between calcium concentration and optical response. This calibration curve can then be stored for subsequent use when making optical measurements of samples having unknown concentrations of calcium.

Each composition described as a calibration solution can be an aqueous solution having a known amount of calcium that is mixed with a calcium-indicating reagent. The calcium-indicating reagent may include at least an indicator that complexes or otherwise interacts with calcium present in the calibration solution to provide a measurable optical response. The calcium-indicating reagent may or may not include other constituent ingredients, such as a pH buffer, a range extender, and the like.

With certain indicator systems, the calcium-indicator complex does not provide a linear optical response with changing calcium concentration. In other words, as the calcium concentration increases, the optical response (e.g., absorbance) does not progressively increase or decrease in a linear fashion. Rather, the optical response may vary non-linearly (e.g., defining a second or higher order polynomial, a power law, an index function curve, a logarithmic curve) as the calcium concentration increases. As a result, measuring the optical response of two calibration solutions would not typically be sufficient to calibrate the optical sensor for the indicator system because the two data points would not capture the nonlinearity of the calibration curve between and outside the two data points.

In accordance with examples of the present disclosure, however, Applicant has discovered that the optical response of the calcium-indicator complex may be linearized to allow a two-point calibration even in situations where the relationship between calcium concentration and the direct optical response is nonlinear. In some implementations, the optical response of a first calibration solution and a second calibration solution are each measured at multiple wavelengths. A ratio of the optical response of each calibration solution at the different wavelengths can be determined. The optical sensor can then be recalibrated based on a linear relationship between calcium concentration and the ratio of the optical response.

Although an optical sensor can be calibrated in number of different ways as discussed herein, in some implementations, an automated calibration method is performed. An automated calibration method may be a technique performed without human intervention. For example, operating under the control of the controller, an optical sensor system may generate calibration solutions for measurement (e.g., controlling one or more pumps and valves), measure the optical response of the calibration solutions, and determine and store calibration information from the calibration solutions. The optical sensor system may subsequently use this calibration information to make calcium concentration measurements from samples having unknown calcium concentrations. In turn, this measured calcium concentration information may be used to control the operating conditions of the system from which the water sample containing the calcium so measured was extracted.

Additional details on example optical sensors and calibration techniques will be described with respect to FIGS. 2-8. However, an example operating environment in which an industrial water may contain calcium desirably measured by an optical sensor according to the techniques of the present disclosure will be described with respect to FIG. 1. In particular, FIG. 1 describes an example cooling water system that contains a recirculating water stream. This water stream may contain calcium, which may be desirably measured using an optical sensor and which may be controlled based on the measurements made by the optical sensor. While FIG. 1 focuses on cooling water as an example industrial calcium-containing water, it should be appreciated that the disclosure is not limited in this effect. Any water that may contain calcium may be used in accordance with the disclosure. Example waters that may be measured and/or control using the systems and techniques of the disclosure include, but are not limited to, heating water systems (e.g., boiler systems), cooling water systems (e.g., systems comprising a cooling tower), pipelines for water transport (e.g., seawater transport, which may be in transport to mining operations), waste water systems (e.g., industrial waste water streams, including those in the petrochemical and mining industries), and the like.

Independent of the source, the aqueous sample being measured may contain any amount of calcium. Typical amounts of calcium that may be found in industrial water samples analyzed according to the disclosure include a calcium concentration falling within a range from 0.5 ppm to 10,000 ppm, such as from 2 ppm to 5000 ppm, from 100 ppm to 3000 ppm, or from 500 ppm to 200 ppm. In some applications, the concentration of calcium in the water to be measured is less than 8,000 ppm, such as less than 5000 ppm, less than 2000 ppm, less than 1000 ppm, or less than 500 ppm.

FIG. 1 is a conceptual diagram of an example industrial water system 10 with optical sensor 100 that can be calibrated and used to measure calcium concentration in water in the system. Industrial water system 10 is illustrated as a cooling water system that includes a cooling tower 102, one or more heat exchanges 104, and a pump 106 that can introduce one or more chemical agents into a cooling water stream being recirculated through the heat exchange (e.g., network of heat exchangers). A controller 136A manages operation of optical sensor 100 while a controller 136B manages operation of the broader industrial water system 10.

Controllers 136A and 136B can be implemented using a single system controller or may be implemented using multiple controllers, which may or may not be communicatively connected together. Accordingly, while system 10 is illustrated as having two controllers 136A and 136B, system 10 including optical sensor 100 may be controlled with a single controller or more controllers without departing from the scope of disclosure. As such, controllers 136A and 136B are collectively referred to as "controller 136" for purposes of discussion.

In operation, controller 136 can control optical sensor 100 to analyze cooling water in the system. For example, controller 136 can control optical sensor 100 to obtain a sample of cooling water from a fluid pathway through which the water is flowing and introduce one or more reagents into the cooling water sample to facilitate optical analysis. The controller can further control optical sensor 100 to emit light into the sample so prepared and detect light from the sample. Controller 136 can determine a concentration of calcium in the sample based on the optical response of the sample (e.g., amount of light absorbed by the sample) with reference to calibration information stored in a memory associated with the controller. The calibration information may be generated as discussed herein.

During operation of system 10, a comparatively hot process stream can pass through a process stream-side of heat exchanger 104 while a comparatively cold cooling water stream passes through a cooling water stream-side of the exchanger. The fluids are separated by a solid wall surface within the heat exchanger to prevent mixing of the fluids. Thermal energy can transfer from the comparatively hot process stream to the comparatively cold cooling water stream, resulting in a reduction in the temperature of the process stream and an increase in the temperature of the cooling water stream. While the example system of FIG. 1 includes only a single heat exchanger 104 for purposes of illustration, a heat exchange network utilizing the concepts of the present disclosure may include multiple heat exchangers (e.g., each configured as heat exchanger 104 is described).

Heat exchanger 104 in the example of FIG. 1 includes a cooling water inlet 108 and a cooling water outlet 110. The heat exchanger also includes a process stream inlet 112 and process stream outlet 114. A cooling water stream 116 can enter heat exchanger 104 through the cooling water inlet 108, flow through one or more divided pathways inside of the heat exchanger, and exit the heat exchanger through the cooling water outlet 110. Likewise, a process stream 118 can enter heat exchanger 104 through the process stream inlet 112, flow through one or more divided pathways inside of the heat exchanger that are separated from the cooling water stream, and exit the heat exchanger through process stream outlet 114. In some configurations, the cooling water stream and the process stream flow in co-current directions through the heat exchanger. In other configurations, the cooling water stream and the process stream flow in countercurrent directions through the heat exchanger. In general, heat exchanger 104 can be implemented using any desired type of heat exchanger design, such as a shell and tube heat exchanger, a plate heat exchanger, or other type of thermal transfer device.

In the illustrated configuration, cooling water stream 116 is delivered to heat exchanger 104 from an upstream cooling tower 102 and recycled back to the cooling tower after passing through the heat exchanger. Cooling water stream 116 may pass through one or more heat exchangers before entering heat exchanger 104 and/or through one or more heat exchangers after passing through heat exchanger 104 before returning to cooling tower 102. At cooling tower 102, thermal energy transferred to the cooling water stream flowing through the heat transfer circuit can be removed and discharged to atmosphere. For example, cooling tower 102 may bring the cooling water stream in direct contact with air, resulting in a reduction in the temperature the cooling water stream through evaporative cooling. The cooling water may be delivered to a sump or reservoir before being drawn out and passed through the heat exchange network.

In addition to water loss through evaporation, cooling water may be periodically removed from the heat exchange system. A discharge line 120 can be used to bleed-off (or "blow down") a portion of the sump or reservoir water while the system is operating. In any case, a "make-up" water line 122 can supply fresh water to the cooling system to make for water losses through evaporation or deliberate dumping.

In practice, a variety of issues may impact the thermal performance of heat exchanger 104 from the cooling water side of the heat exchanger. For example, if the cooling water contains a high level of solids (e.g., silt, debris) the solids may partially or fully plug the cooling water fluid pathway through heat exchanger 104. As an example, the cooling water may contain chemical constituents that cause deposits to form on the internal surfaces of heat exchanger 104 contacted by the cooling water.

For example, the evaporation of cooling water can lead to the concentration of salts (e.g., calcium, sodium, magnesium) in the cooling water stream recycled through the system. These salts can form scale fouling on surfaces of heat exchanger 104 contacted by the cooling water. The term "scale fouling" refers to fouling of a heat exchange surface by particulate matter from or formed in the cooling water including, but not limited to, constituents such as calcium carbonate, calcium phosphate, and calcium sulfate. The amount of calcium present in the cooling water may correspond to the amount and extent to which calcium-containing scale fouling occurs within system 10. For these and other reasons, the amount of calcium present in the cooling water may be measured using optical sensor 100.

To help reduce or eliminate potential fouling conditions in the cooling water stream passing through the heat transfer network, one or more chemicals may be added to the cooling water to inhibit formation and/or deposition of foulants. In the configuration of FIG. 1, system 10 includes one or more pump 106A-106Z (collectively referred to as "pump 106") fluidly connected to one or more respective chemical additive reservoirs 124A-124Z (collectively referred to as "chemical reservoir 124"). Pump 106 can operate to add one or more chemicals to the cooling water that are selected to inhibit the formation and/or deposition of foulants on surfaces contacted by the cooling water. For example, pump 106 may add one or more calcium control agents to the cooling water. The calcium control agent(s) can react with calcium present in the cooling water, e.g., to form a calcium-containing precipitate that can be removed from the water and/or to deactivate calcium present in the water such that the calcium is not available to generate scale fouling.

Example chemical additives that may be injected into the cooling water include, but are not limited to, polymers (dispersants and scale inhibitors), organophosphorus compounds such as phosphinosuccinic oligomer (PSO, scale and corrosion inhibitor), orthophosphate (corrosion inhibitor), polyphospahtes (scale and corrosion inhibitors), biocides, and combinations thereof. Additionally or alternatively, one or more chemical additives may be injected into the cooling water to adjust the pH of the cooling water. Examples of pH adjusting control agents include mineral acids, organic acids, and inorganic bases. In some examples, one or more scale polymers is injected into the cooling water as a chemical additive such as an acrylic acid, 2-acrylamido-2-methyl propane sulfonate copolymer (AA/AMPS), a (meth)

acrylic acid, a sulfoalkyl(meth)acrylamide copolymer, and the like, including combinations thereof.

In the illustrated configuration of FIG. 1, pump 106 is illustrated as adding chemical additive to the cooling water between cooling tower 102 and heat exchanger 104. In practice, the chemical additive may be introduced to the cooling water stream at any suitable location, such as a sump associated with the cooling tower. Moreover, while system 10 in FIG. 1 illustrates a single pump 106 fluidly coupled to a single chemical additive reservoir 124, pump 106 may be in selective fluid communication with multiple reservoirs containing different chemicals and/or system 10 may include multiple pumps each configured to introduce a different chemical into the cooling water. By providing multiple different chemical additives, include some or all of those discussed above, the type of chemical introduced into the cooling water can be changed based on changing conditions of the cooling water.

As briefly discussed above, system 10 in the example of FIG. 1 includes controller 136. Controller 136 can be communicatively connected to the controllable components of system 10 to manage the overall operation of the system. For example, controller 136 can be communicatively connected to optical sensor 100, cooling tower 102, pump 106, and any other sensors or process control devices in the system (e.g., to set the flow rate and/or temperature of the process stream and/or cooling water stream flowing through the system). In some implementations, optical sensor 100 is controlled by a first controller 136A while the processing components of system 10 are controlled by a second controller 136B.

Controller 136 includes processor 138 and memory 140. Controller 136 communicates with communicatively connected components via a wired or wireless connection, which in the example of FIG. 1 is illustrated as a wired connection. Control signals sent from and received by controller 136 can travel over the connection. Memory 140 stores software for running controller 136 and may also store data generated or received by processor 138, e.g., from optical sensor 100. For example, memory 140 can store calibration data 142 generated based on measurements of calibration solutions made by optical sensor 100 during calibration. Controller 136 can reference calibration data 142 to process optical measurements of cooling water made by optical sensor 100 during operation, e.g., to determine a measure calcium concentration in the cooling water. Processor 138 can run software stored in memory 140 to manage the operation of system 10.

Controller 136 may be implemented using one or more controllers, which may be located at the facility site containing optical sensor 100 and/or remote therefrom. Controller 136 may communicate with one or more remote computing devices 144 via a network 146. For example, controller 136 may communicate with a geographically distributed cloud computing network, which may perform any or all of the functions attributed to controller 136 (e.g., controller 136A and/or controller 136B) in this disclosure.

Network 146 can be configured to couple one computing device to another computing device to enable the devices to communicate together. Network 146 may be enabled to employ any form of computer readable media for communicating information from one electronic device to another. Also, network 146 may include a wireless interface, and/or a wired interface, such as the Internet, in addition to local area networks (LANs), wide area networks (WANs), direct connections, such as through a universal serial bus (USB) port, other forms of computer-readable media, or any combination thereof. On an interconnected set of LANs, including those based on differing architectures and protocols, a router may act as a link between LANs, enabling messages to be sent from one to another. Communication links within LANs may include twisted wire pair or coaxial cable, while communication links between networks may utilize analog telephone lines, full or fractional dedicated digital lines, Integrated Services Digital Networks (ISDNs), Digital Subscriber Lines (DSLs), wireless links including cellular and satellite links, or other communications links. Furthermore, remote computers and other related electronic devices may be remotely connected to either LANs or WANs via a modem and temporary telephone link.

Optical sensor 100 may be implemented in a number of different ways in system 10. In the example shown in FIG. 1, optical sensor 100 is positioned in-line with a fluid pathway to draw fluid out of the pathway for measuring calcium in fluid flowing through the fluid pathway. In various examples, a pipe, tube, or other conduit may be connected between the fluid pathway and a flow chamber of optical sensor 100. In such examples, the conduit can fluidly connect the flow chamber (e.g., an inlet of the flow chamber) of optical sensor 100 to the fluid pathway. As fluid moves through the fluid pathway, a portion of the fluid may enter the conduit and pass adjacent one or more optical emitters and one or more optical detectors positioned within a fluid chamber, thereby allowing optical sensor 100 to determine an optical response of a titrated sample. In yet other examples, optical sensor 100 may be used to optically analyze a sample that does not flow through a flow chamber of the optical sensor. For example, optical sensor 100 may be implemented as an offline monitoring tool that requires filling (e.g., manually or automatically) the optical sensor with a fluid sample, a titrant, and any desired indicator and/or reagents.

Figure 2:
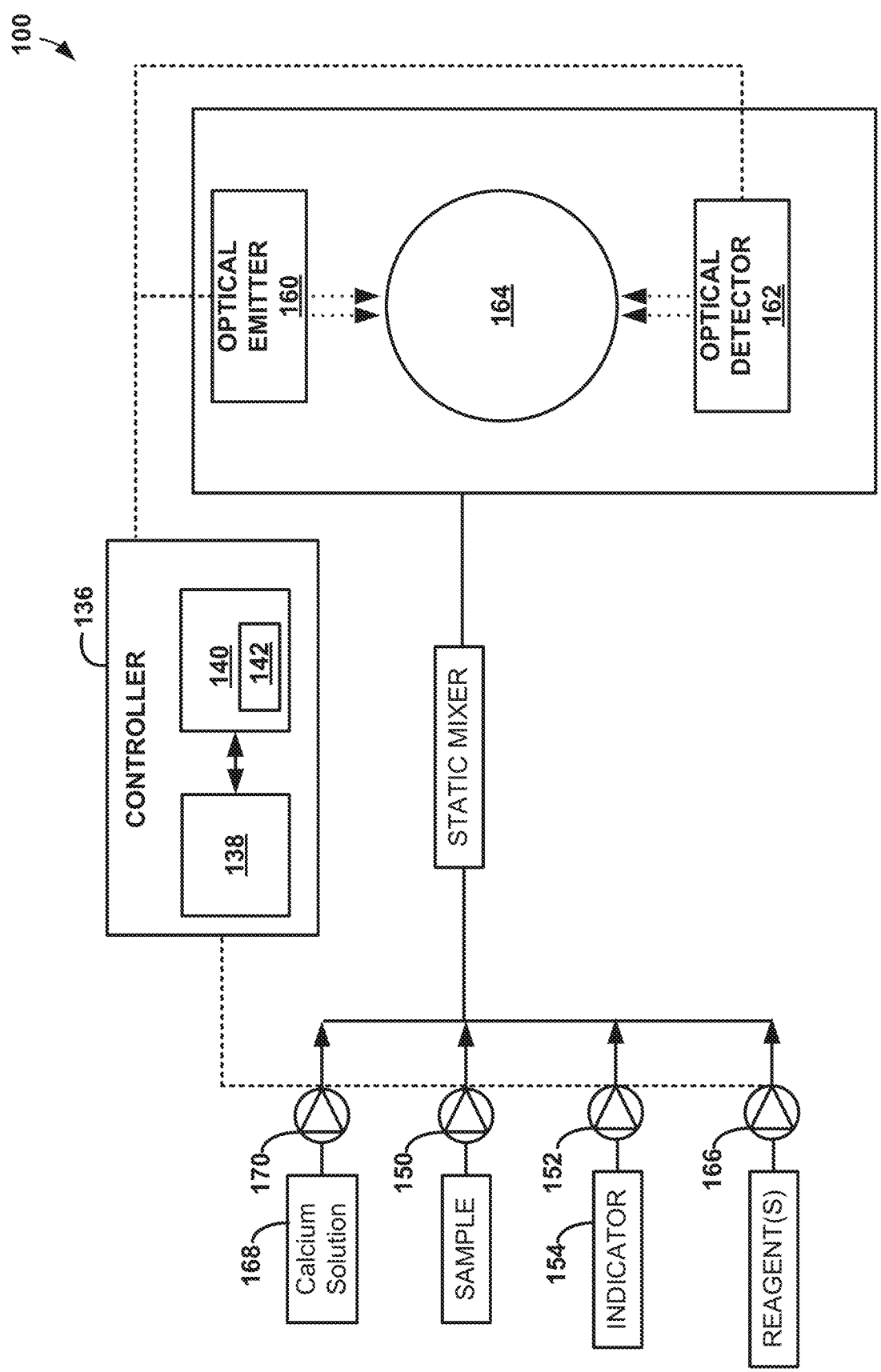
FIG. 2 is a block diagram of an example configuration of an optical sensor that may be used to measure calcium in an industrial water sample.

FIG. 2 is a block diagram of an example configuration of optical sensor 100 that may be used to measure calcium in an industrial water sample. Optical sensor 100 is illustrated in the form of a system that includes an optical emitter and an optical detector as well as hardware for extracting a water sample and mixing one or more reagents with the sample prior to optical analysis. In other configurations, optical sensor 100 may be implemented without the reagent and mixing features of FIG. 2 or may have other configurations than the specific example illustrated. Moreover, optical sensor 100 in FIG. 2 is illustrated as being controlled by controller 136 discussed above with respect to FIG. 1. Controller 136 can be communicatively connected to the controllable components within optical sensor 100 to send and/or receive data and control signals to/from the components. However, the functions described as being performed by controller 136 in FIG. 2 (e.g., with respect to calibration) may be performed by a different system controller, one or more remote computing devices 144, and/or other controller hardware and/or software.

In the example of FIG. 2, optical sensor 100 is illustrated as including a sample pump 150 that can operate to provide a sample containing an unknown concentration of calcium, such as an aqueous sample from a flowing stream of industrial water. Sample pump 150 can extract a sample of water from a fluid pathway in system 10 for analysis. Optical sensor 100 can also include an indicator pump 152 that pumps indicator from a source of indicator 154 (e.g., reservoir or container containing indicator) for mixing with the sample of water for subsequent optical analysis. The indicator can complex or otherwise react with calcium present in the water to produce a measurable optical response, the extent of which varies in response to the amount of calcium present in the sample under analysis.

To measure the optical response of the sample containing the calcium-indicator reaction product (e.g., a calcium-indicator complex), optical sensor 100 may include one or more optical emitters 160 and one or more optical detectors 162 optically connected to a sample receiving space 164 for optical analysis. Sample receiving space 164 may be an optical cell that receives and holds a static portion of fluid that undergo optical analysis, for example, in a stop flow configuration with the sample subsequently being discharged. As another example, sample receiving space 164 may be or include a fluid conduit through which a flowing stream of fluid passes with optical analysis being performed on the flowing stream of fluid.

Reaction between the one or more indicators introduced into the sample and one or more of the analytes of unknown concentration in the sample, at least one of which is calcium, can produce an optically detectable change. The concentration of calcium can be proportional to the measured optical response of the sample. For example, the optical response may be a colorimetric change that occurs through when a complex is formed between calcium in the sample and the indicator. The reaction between the indicator and calcium may occur in or upstream of sample receiving space 164 and be detected by measuring an absorbance of the sample.

In some examples, optical sensor 100 is configured to introduce one or more additional reagents to a sample undergoing optical analysis. The one or more additional reagents may be present with indicator and introduced simultaneously with the indicator or may be introduced separately from the indicator. In the example of FIG. 2, optical sensor is illustrated as including one or more additional reagent pumps 166 fluidly connected to one or more additional sources of reagent. In other examples, the indicator 154 and other desired reagents may be mixed and/or stored together and delivered through single pump 152 instead of being separately introduced.

Example chemical reagents that may be added to the fluid sample in addition to the indicator include, but are not limited to, a pH adjuster and/or buffer, a reaction catalyst, a sequestrant, a surfactant, a range extender or a combination thereof. For example, controller 136 may control the addition of a pH adjustor to the sample undergoing analysis so the sample is within a pH range where the calcium-indicator complex forms. As another example, controller 136 may control the addition of a range extender that complexes with some but not all of the calcium present (or expected to be present) in the sample, allowing the calcium indicator to complex with the remaining calcium present in the sample without saturating the ligands of the indicator. The specific types of indicators and/or reagents added to the sample will vary depending on the specific application of the system.

In some examples, such as implementations when optical sensor 100 is configured to automatically perform recalibration, the optical sensor 100 may include one or more calcium-containing solutions 168, each having a known concentration of calcium. A pump 170 can be fluidly connected to the one or more calcium solutions and configured to control addition of a target amount of the calcium solution, e.g., for combining with indicator and/or reagents to generate a calibration solution.

For example, in some implementations, each of the first and second calibration solutions used to calibrate the optical sensor are generated onsite where optical sensor 100 is located with system 10, e.g., with an automated calibration solution generator system. The automated calibration solution generator may include one or more pumps fluidly connected to one or more aqueous solutions of calcium and the calcium-indicating reagent. For example, the automated calibration solution generator may include one or more pumps fluidly connected to a first reservoir containing an aqueous solution with a first calcium concentration (effective to provide the first known calcium concentration upon being mixed with the calcium-indicating reagent) and to a second reservoir containing an aqueous solution with the second known calcium concentration (effective to provide the second known calcium concentration upon being mixed with the calcium-indicating reagent). The automated calibration solution generator may also include one or more pumps fluidly connected a third reservoir containing the calcium-indicating reagent.

Operating under the control of a controller (e.g., controller 136), the automated calibration solution generator may mix a predetermined amount of the calcium-containing liquid from the first reservoir with a predetermined amount of the calcium-indicating reagent, thereby generating the first calibration solution that is delivered to sample receiving space 164 of optical sensor 100 for optical analysis. The automated calibration solution generator may similarly mix a predetermined amount of the calcium-containing liquid from the second reservoir with a predetermined amount of the calcium-indicating reagent, thereby generating the second calibration solution that is delivered to sample receiving space 164 of optical sensor 100 for optical analysis.

As mentioned above, optical sensor 100 can include one or more optical emitters that emit light into each sample over a plurality of wavelengths and one or more detectors that detect light from the fluid sample over a plurality of wavelengths, which may be the same as or different than the wavelengths emitted into the fluid sample. In different examples, the one or more optical detectors may detect light passing through the fluid sample under analysis (e.g., transmittance, absorbance), light scattered by the fluid sample, a fluorescent response of the fluid sample, or yet other optical response of the fluid sample. In one specific example, optical sensor is configured to detect the absorbance of the fluid sample under analysis. As is known by those of ordinary skill in the art, absorbance is a measure of how much incident light is absorbed when it travels in a sample while transmittance measures how much of the light is transmitted through the sample. According, an optical sensor according to the disclosure may measure absorbance and/or transmittance to provide the same function.

Optical emitter 160 may emit light at multiple wavelengths into a sample under analysis and optical detector 162 may further detect light across multiple wavelengths from the sample. Controller 136 can then use a spectral characteristic associated with one or more of the multiple of wavelengths to determine the concentration of calcium in the sample.

For example, operating under the controller of controller 136, optical emitter 160 can direct light into a fluid sample and optical detector 162 can receive transmitted light on the opposite side of the fluid sample. Optical emitter 160 may include at least one optical emitter that emits radiation over multiple wavelengths, such as multiple wavelengths within a specified wavelength range. In some examples, optical emitter 160 emits radiation over continuous range of wavelengths. In other examples, optical emitter 160 emits radiation at a plurality of discrete wavelengths. For example, optical emitter 160 may emit at two, five, ten, fifty, or more discrete wavelengths. Example light sources that can be used as optical emitter 160 include one or more light emitting diodes (LEDS), lasers, and/or lamps.

The specific wavelength(s) over which optical emitter 160 emits light into the fluid sample under analysis may vary depending on the specific indicator and/or reagents combined with the calcium-containing fluid sample. In some examples, optical emitter 160 is configured to emit light over a plurality of wavelengths at or near different absorbance maxima for the calcium-indicator complex in the sample under analysis. For example, a wavelength of light emitted into the sample may be or include an absorbance maxima for a calcium-indicator reaction product. The absorbance maxima can be determined by optically analyzing a reference solution in which calcium is reacted with the selected indicator and/or reagents to be subsequently used in practice. Optical emitter 160 can then be configured to emit light at the determined absorbance maxima and/or selected wavelengths overlapping with such absorbance maxima.

Light emitted by optical emitter 160 propagates through the sample under analysis and may be detected by optical detector 162. The amount of radiation detected by optical detector 162 depends on the contents of the sample. If the sample has a certain concentration of calcium, indicator, and/or reagents, optical detector 162 can detect a certain level of radiation emitted from optical emitter 160. However, if the sample has a different concentration, optical detector 162 may detect a different level of radiation emitted from optical emitter 160.

Optical detector 162 includes at least one optical detector that detects radiation over one or more wavelengths emitted by optical emitter 160. The wavelengths detected by optical detector may encompasses the same wavelengths emitted by optical emitter 160 or may be a broader or narrower ranged than the wavelengths emitted by the optical emitter. When performing absorbance and/or transmittance measurements, optical detector 162 may detect the same wavelength(s) of light emitted into the sample by optical emitter 160. In some examples, optical detector 162 detects wavelengths within the visible light spectrum and/or ultraviolet spectrum. For example, optical detector 162 may detect wavelengths of light over a range that includes from about 390 nm to 700 nm, such as from 400 nm to 675 nm, from 450 nm to 650 nm, or from 500 nm to 600 nm. Optical detector 162 may detect a continuous spectrum within the foregoing ranges or may detect discrete wavelengths of light within the spectrum. Optical detector 162 may detect light at two or more wavelengths.

In some examples, optical detector 162 is implemented using an optical spectrometer that measures the intensity of light as a function of wavelength or of frequency. Optical detector 162 may include one or more photodetectors such as, e.g., photodiodes or photomultipliers, for converting optical signals into electrical signals.

As briefly mentioned a variety of different indicators may be used to complex with calcium and provide a measurable optical response corresponding to the amount of calcium present in the sample. One example indicator that can be used to complex with calcium in a sample under analysis is di sodium 2,7-bis[(4-chloro-2-phosphonophenyl)azo]-4,5-dihydroxy-2,7-naphthalenedisulfonate (Chlorophosphonazo-III) [1914-99-4], and salts thereof. Chlorophosphonazo-III has the following structure:

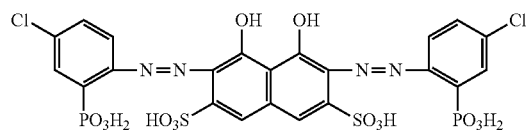

Other example indicators that may be used to optically measure calcium include disodium 3-[(4-chloro-2-phosphonophenyl)azo]-4,5-dihydroxy-2,7-naphthalenedisulfonate (Chlorophosphonazo-I) [1938-82-5], disodium 3-3-[(acetylphenyl)azo]-6-[(4-chloro-2-phosphonophenyl)azo]-4,5-dihydroxy-2,7-naphthalenedisulfonate (Chlorophosphonazo-mA) [86167-87-5], and salts thereof. Yet other example indicators that may be used to optically measure calcium include Eriochrome Black T, o-cresolphthalein complexone, and Arsenazo III.

The calcium-indicator complex may exhibit an optical response that is non-linear across a range of calcium concentrations. For example, the optical response (e.g., absorbance) of the calcium-indicator may not increase or decrease linearly with changing calcium concentration but may exhibit a curve over a range of calcium concentrations of potential interest.

When using an indicator such as those indicated above, optical emitter 160 may emit light within the visible light spectrum, e.g., falling within the range from about 390 nm to 700 nm. For example, optical emitter 160 may emit light within a range from 400 nm to 675 nm, such as from 450 nm to 650 nm, or from 500 nm to 600 nm. For example, optical emitter 160 may emit light within a first wavelength falling within a range from 625 nm to 700 nm and/or at a second wavelength falling within a range from 475 nm to 575 nm. Optical detector 162 may be configured to detect light at any of the wavelength(s) emitted by optical emitter 160.

As specific examples, optical emitter 160 may emit light at a first wavelength of approximately 668 nm (e.g., plus or minus 15 nm) and at a second wavelength of approximately 521 nm (e.g., plus or minus 15 nm). A ratio of absorbances at these two wavelengths (or wavelength ranges) can be linearized (e.g., based on the power law, or exponential function, or polynomial of higher than two orders) so that the ratio is linearly proportional to the variation of calcium concentration in the water sample under analysis. In addition, such an absorbance ratio between the two wavelengths has been found, in some implementations, to not change, or change only a limited amount (e.g., plus or minus 10 percent or less) when the mixing ratio of the sample to the reagent varies. Further, such an absorbance ratio is generally not susceptible to interference due to water chemistry and/or water treatment programs typically used in commercial practice.

Independent of the specific wavelength or wavelength ranges selected for the absorbance measurement, ratioing the absorbance measurements can provide a signal that exhibits less deviation and noise than a signal absorbance measurement. This can allow lower calcium levels to be detected than when using a single wavelength (or wavelength range) absorbance measurement. This can be beneficial independent of the number of calibration measurements taken to calibrate the optical sensor (e.g., even when using more than two calibration measurements/solutions).

Controller 136 controls the operation of optical emitter 160 and receives signals concerning the amount of light and/or frequency or wavelength(s) of light detected by optical detector 162. In some examples, controller 136 processes signals received from optical detector 162 during analysis of a water sample containing an unknown concentration of calcium and determines a concentration of calcium in the sample based on calibration curve data 142 stored in memory.

While controller 136 described with respect to FIG. 1 as controlling system 10 is also illustrated as the controller controlling optical sensor 100, the optical sensor may have a separate controller from one or more system controllers controlling the overall operation of system 10. Accordingly, it should be appreciated that the computing functionality attributed to controller 136 in this disclosure may be performed on any one or more controllers associated with the system, be it physically onsite or remotely located, and the functionalities described herein are not limited to being performed on any specific hardware device.

In either case, a memory 140 associated with controller 136 (e.g., contained within or physically remote from and providing data accessible to a processor) may store data 142 representative of one or more calibration curves used by controller 136 to determine a concentration of calcium in a fluid medium under analysis. Calibration curve data 142 may relate light detected by optical detector 162 to a concentration of calcium in the fluid under analysis. In some examples, calibration curve data 142 is in the form of coefficients for an equation that relates light measurements taken by optical detector 162 to calcium concentration information. For example, the equation may be a first-order equation having a slope coefficient and an intercept coefficient, each of which are stored in memory and referenced by controller 136 to convert light information measured by optical detector 162 to calcium concentration information.

To help increase the accuracy of the measured calcium concentrations determined by optical sensor 100, the optical sensor may undergo periodic recalibration. For example, calibration curve data 142 stored in memory and used by controller 136 to convert measured optical response data to measured calcium concentration data may include a stored calibration curve intercept coefficient and a stored calibration curve slope coefficient. During recalibration, the stored calibration curve slope and intercept coefficients may be re-determined and new coefficients stored in memory.

Figure 3:
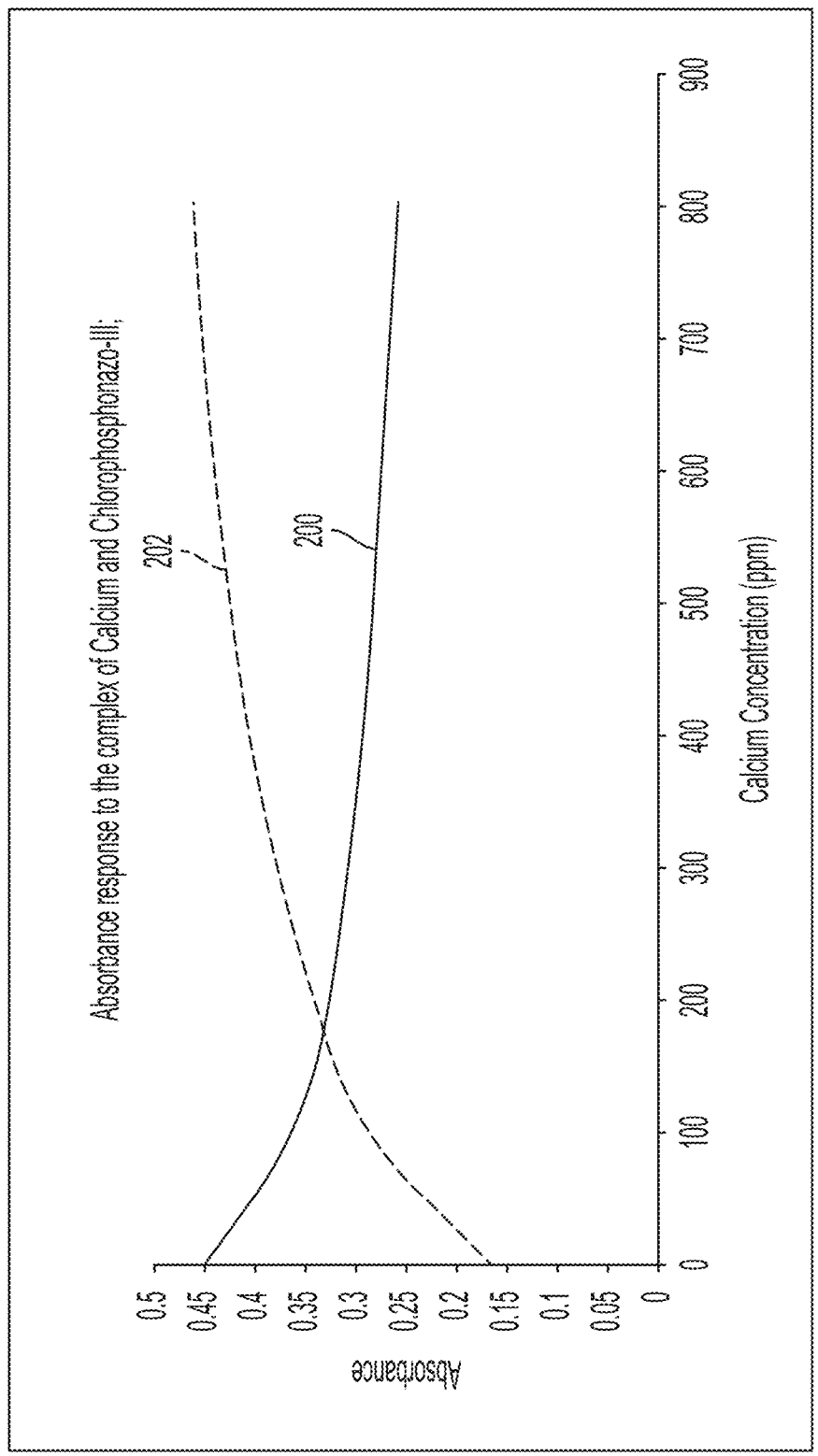
FIG. 3 is a plot of the absorbance response of an example calcium-containing solution mixed with Chlorophosphonazo-III at two example wavelengths.

With certain indicator systems, such as when using Chlorophosphonazo-III as an indicator, the calcium-indicator complex does not provide a linear optical response with changing calcium concentration over a range of interest. Rather, the optical response can vary nonlinearly (e.g., such that the optical response does not progressively increase or decrease) as the calcium concentration increases. FIG. 3 is a plot of the absorbance response of an example calcium-containing solution mixed with Chlorophosphonazo-III at two example wavelengths: a first wavelength of 521 nm (line 200) and a second wavelength of 668 nm (line 202). The plot illustrates how the optical response, specifically absorbance in the illustrated plot, of the calcium-indicator complex in the example studied does not vary linearly across the range of calcium concentrations evaluated but curves at both wavelengths to define a second-order relationship between calcium concentration and absorbance.

In accordance with examples of the present disclosure, however, Applicant has discovered that the optical response of the calcium-indicator complex may be linearized to allow a two-point calibration even in situations where the relationship between calcium concentration and the direct optical response is nonlinear. In some implementations, the optical response of a first calibration solution and a second calibration solution are each measured at multiple wavelengths. A ratio of the optical response of each calibration solution at the different wavelengths can be determined. The optical sensor can then be recalibrated based on a linear relationship between calcium concentration and the ratio of the optical response.

Figure 4:
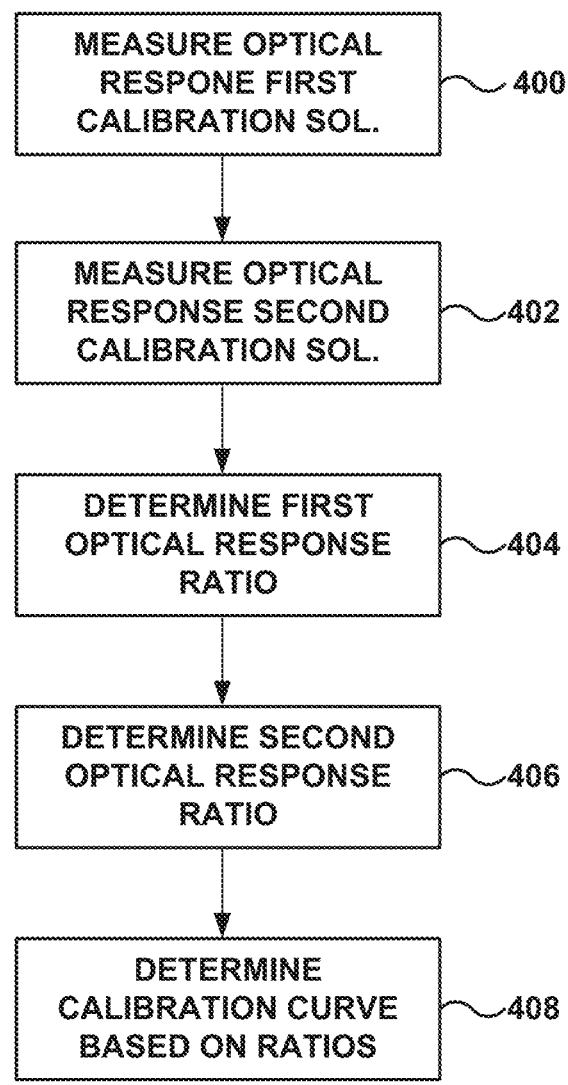
FIG. 4 is a flow diagram of an example technique for calibrating an optical sensor.

FIG. 4 is a flow diagram of an example technique for recalibrating an optical. The technique of FIG. 4 is described with reference to optical sensor 100 in FIGS. 1 and 2, although can be performed in other systems and with other sensor configurations.

With reference to FIG. 4, the example technique includes measuring an optical response of a first calibration solution with optical sensor 100 (400). The first calibration solution can be a mixture of the calcium-indicator reagent and a first calcium stock solution (which has a concentration effective to provide the first calcium concentration after combining with the calcium-indicator reagent, for example in an approximately 2:1 ratio). In different implementations, optical sensor 100 may automatically generate and/or supply the first calibration solution to sample receiving space 164, or an operator can manually fill the sample receiving space with the calibration solution. The first calibration solution may be selected to have a first known concentration of calcium.

In general, when performing two-point calibration, two calibration solutions having different known calcium concentrations may be used. The specific calcium concentrations for the two calibration solutions may encompass or bound a range of calcium concentrations expected to be observed by the optical sensor in subsequent operation. Accordingly, the first calibration solution may be selected to have a first known concentration of calcium at a comparatively high end or a comparatively low end of the calibration curve. In some implementations, the first calibration solution has a first known calcium concentration less than 100 ppm calcium, such as less than 10 ppm calcium. The first known calcium concentration may be greater than zero (e.g., such that there is a measurable amount of calcium present in the sample) or the first known concentration of calcium may be zero. In this latter example, the first calibration solution may be a blank solution not having any calcium-containing solution added to the calibration solution. Rather, the first calibration solution may be formed of the other chemical components added to a water sample during analysis (other reagent(s), indicator, etc. used during optical analysis) and/or water substantially devoid of calcium (e.g., deionized water).

With the first calibration solution positioned within sample receiving space 164, controller 136 can control optical emitter 160 to emit light into the first calibration solution and control optical detector 162 to detect light transmitted through the first calibration solution. Controller 136 can control the one or more optical emitters 160 to emit light at two or more wavelengths, including at a first wavelength and a second wavelength. The two or more wavelengths of light used to optically analyze the first calibration solution may be selected as discussed above. In some examples, controller 136 controls optical emitter 160 to sequentially interrogate the sample with the first wavelength of light followed by the second wavelength of light. For example, the one or more optical emitters 160 may emit light across a spectrum encompassing the first wavelength and the second wavelength of interest.

Optical detector 162 can detect an optical response of the first calibration solution in response to the light emitted by optical emitter 160. When the optical response corresponds to an absorbance of the first calibration solution or transmittance therethrough, optical detector 162 may detect an amount of light emitted by optical emitter 160 and passing through sample receiving area 164 with the first calibration solution contained therein. The amount of light detected by optical detector 162 in response to optical emitter 160 emitting light at the first wavelength can provide a first measured optical response (e.g., absorbance, transmittance) for the first calibration solution. The amount of light detected by optical detector 162 in response to optical emitter 160 in the light at the second wavelength can provide a second measured optical response (e.g., absorbance, transmittance) for the first calibration solution. Controller 136 can store the measured optical responses of the first calibration solution in memory 140.

The technique of FIG. 4 also includes measuring an optical response of a second calibration solution by optical sensor 100 (402). The second calibration solution can be a mixture of the calcium-indicator reagent and a second calcium stock solution (which has a concentration effective to provide the second calcium concentration after combining with the calcium-indicator reagent, for example in an approximately 2:1 ratio). Again, optical sensor 100 may automatically generate and/or supply the first calibration solution to sample receiving space 164, or an operator can manually fill the sample receiving space with the calibration solution. The second calibration solution may be selected to have a second known concentration of calcium.

The calcium concentration of the second calibration solution can be selected in coordination with the first calibration solution, e.g., so the two calibration solutions encompass or bound a range of calcium concentrations expected to be observed by the optical sensor in subsequent operation. While the specific calcium concentration in the second calibration solution may vary, e.g., depending on the concentration of calcium expected to be observed in water samples during subsequent use of the optical sensor, in some examples the calcium concentration is greater than 10 ppm calcium, such as greater than 50 ppm calcium, greater than 100 ppm calcium, or greater than 250 ppm calcium. For example, the calcium concentration of the second calibration solution may be a value falling within a range from 10 ppm calcium to 2000 ppm calcium, such as from 50 ppm calcium to 1000 ppm calcium, or from 100 ppm calcium to 500 ppm calcium. The calcium concentration in the second calibration solution may differ from the calcium concentration in the first calibration solution by at least 10 ppm calcium, such as by at least 50 ppm calcium, or by at least 100 ppm calcium.

The second calibration solution may be formed of a calcium-containing solution in an amount, once diluted, effective to provide any of the foregoing described calcium concentrations. The second calibration solution may also contain other chemical components added to a water sample during analysis (other reagent(s), indicator, etc. used during optical analysis). These other chemical components may be the same ones also present in the first calibration solution.

With the second calibration solution positioned within sample receiving space 164, controller 136 can control optical emitter 160 to emit light into the second calibration solution and control optical detector 162 to detect light transmitted through the second calibration solution. Controller 136 can control the one or more optical emitters 160 to emit light at two or more wavelengths, including at the first wavelength and the second wavelength used to optically interrogate the first calibration solution. In other words, optical emitter 160 may emit light at the same two wavelengths (optionally along with other wavelengths) emitted into the first calibration solution. In some examples, controller 136 controls optical emitter 160 to sequentially interrogate the sample with the first wavelength of light followed by the second wavelength of light. For example, the one or more optical emitters 160 may emit light across a spectrum encompassing the first wavelength and the second wavelength of interest.

Optical detector 162 can detect an optical response of the second calibration solution in response to the light emitted by optical emitter 160. When the optical response corresponds to an absorbance of the second calibration solution or transmittance therethrough, optical detector 162 may detect an amount of light emitted by optical emitter 160 and passing through sample receiving area 164 with the second calibration solution contained therein. The calcium-indicator complex within the second calibration solution may absorb light, with the amount of light absorbed dependent on the amount of calcium in the calibration solution and the wavelength of light emitted into the calibration solution.

The amount of light detected by optical detector 162 in response to optical emitter 160 emitting light at the second wavelength can provide a second measured optical response (e.g., absorbance, transmittance) for the second calibration solution. The amount of light detected by optical detector 162 in response to optical emitter 160 in the light at the second wavelength can provide a second measured optical response (e.g., absorbance, transmittance) for the second calibration solution. Controller 136 can store the measured optical responses of the second calibration solution in memory 140.

To recalibrate optical sensor 100 based on the optical response measurements of the first and second calibration solutions, processor 138 of controller 136 can execute instructions to determine a first optical response ratio for the first calibration solution (404). The first optical response ratio may be a ratio of the first measured optical response for the first calibration solution (optical response measured at the first wavelength) to the second measured optical response for the first calibration solution (optical response measured at the second wavelength). In one example, the first optical response is divided by the second optical response. In another example, the second optical response is divided by the first optical response. The first optical response ratio can be stored in memory 140 associate with controller 136.

Processor 138 of controller 136 can also execute instructions to determine a second optical response ratio for the second calibration solution (406). The second optical response ratio may be a ratio of the first measured optical response for the second calibration solution (optical response measured at the first wavelength) to the second measured optical response for the second calibration solution (optical response measured at the second wavelength). In one example, the first optical response is divided by the second optical response. In another example, the second optical response is divided by the first optical response. In instances where the first optical response ratio for the first calibration solution is determined by dividing the second optical response by the first optical response for that calibration solution, the second optical response ratio for the second calibration solution may similarly be determined by dividing the second optical response by the first optical response for the second calibration solution. The second optical response ratio can be stored in memory 140 associate with controller 136.

Controller 136 can determine a linear calibration curve relating the optical response measurement made by optical sensor 100 to a corresponding calcium concentration using the optical response ratios and known calcium concentrations from the first and second calibration solutions. Different techniques have been identified to provide a linear relationship between the known calcium concentrations of the calibration solutions and the optical response ratios of those solutions.

In one implementation, controller 136 determines a calibration curve relating a square root of calcium concentration to optical response ratio. For example, the square root of the known calcium concentration of each calibration solution may be plotted (e.g., on the Y-axis) against the optical response ratio for that calibration solution (e.g., on the X-axis). Each calibration solution may therefore yield a data point (with X, Y coordinates), providing two data points that can define a calibration curve or line therebetween. This calibration curve may be sufficiently linear between the ranges of known calcium concentrations in the two calibration solutions to provide linear calibration curve data 142 that can be stored for subsequent use by optical sensor 100 in analyzing samples having unknown calcium concentrations.

In another implementation, controller 136 determines a calibration curve relating calcium concentration to a log (e.g., natural log) of the optical response ratio. For example, the known calcium concentration of each calibration solution may be plotted (e.g., on the Y-axis) against the natural log of the optical response ratio for that calibration solution (e.g., on the X-axis). Each calibration solution may therefore yield a data point (with X, Y coordinates), providing two data points that can define a calibration curve or line therebetween. This calibration curve may be sufficiently linear between the ranges of known calcium concentrations in the two calibration solutions to provide linear calibration curve data 142 that can be stored for subsequent use by optical sensor 100 in analyzing samples having unknown calcium concentrations.

Processor 138 executing instructions stored on memory 140 can determine calibration curve data 142 based on analysis of the data points relating known calcium concentration to a corresponding measured optical response ratio and defining the linear calibration curve (408). For example, processor 138 may perform a curve fitting process such as linear regression to determine a relationship between the known calcium concentration and corresponding measured optical response ratio for each of the calibration solutions. The determined relationship (and/or coefficients associated therewith) can then be stored as calibration curve data 142. Controller 136 may employ any suitable statistical software package such as, e.g., Minitab, Excel, or the like, to generate calibration curve data 142.

In one example, controller 136 may fit a curve representing a square root of known calcium concentration values plotted on the y-axis of the graph with corresponding measured optical response ratios plotted on the x-axis of the graph. A first order curve having the form $y=m*x+b$ can be fit to the data, where y is the square root of calcium concentration, x is the measured absorbance ratio, m is a slope coefficient, and b is an intercept coefficient. The slope and intercept values can be stored as calibration curve data 142 in memory 140.

In another example, controller 136 may fit a curve representing known calcium concentration values plotted on the y-axis of the graph with a log (e.g., natural log) of corresponding measured optical response ratios plotted on the x-axis of the graph. A first order curve having the form $y=m*x+b$ can be fit to the date, where y is the calcium concentration, x is the log of the measured absorbance ratio, m is a slope coefficient, and b is an intercept coefficient. The slope and intercept values can be stored as calibration curve data 142 in memory 140. When performing an exponential curve fit according to this example, each calibration solution may have a known calcium concentration greater than zero.

In executing a calibration technique, such as the calibration technique discussed above with respect to FIG. 4, the first and second calibration solutions may be manually created by an operator and inserted into sample receiving space 164 for optical analysis. Alternatively, one or both of the calibration solutions may be automatically generated by optical sensor 100. For example, depending on the configuration of optical sensor 100, controller 136 may control various valves, pumps, and/or other controllable components to selectively add calcium-containing solution, indicator, reagents, and/or other constituent components of a calibration solution together and provide the resulting calibration solution to sample receiving space 164 for analysis. Controller 136 can control the optical sensor to sequentially generate and analyze the different calibration solutions, each having a different known calcium concentration.

While an example calibration technique has been described with respect to FIG. 4, it should be appreciated that a calibration technique according to disclosure is not limited to the specific order described with respect to FIG. 4. For example, the discussion of a first calibration solution as being one having a comparatively low concentration of calcium and a second calibration solution as being one having a comparatively high concentration of calcium is for purposes of illustration. A calibration solution having any known calcium concentration can be measured in any order. Likewise the processing steps associated with determining optical response ratios and calibration curve data need not be performed in the sequential order described with respect to FIG. 4. Moreover, although the example technique of FIG. 4 provides processing and resource advantages when executed using only two calibration solutions, it should be appreciated that a calibration may be performed using more than two calibration solutions (e.g., three, four, or more) each having a different known calcium concentration than each other calibration solution. In general, using more calibration solutions to provide additional calibration measurements may increase the accuracy of the calibration curve data 142 generate during calibration.

Figure 5:
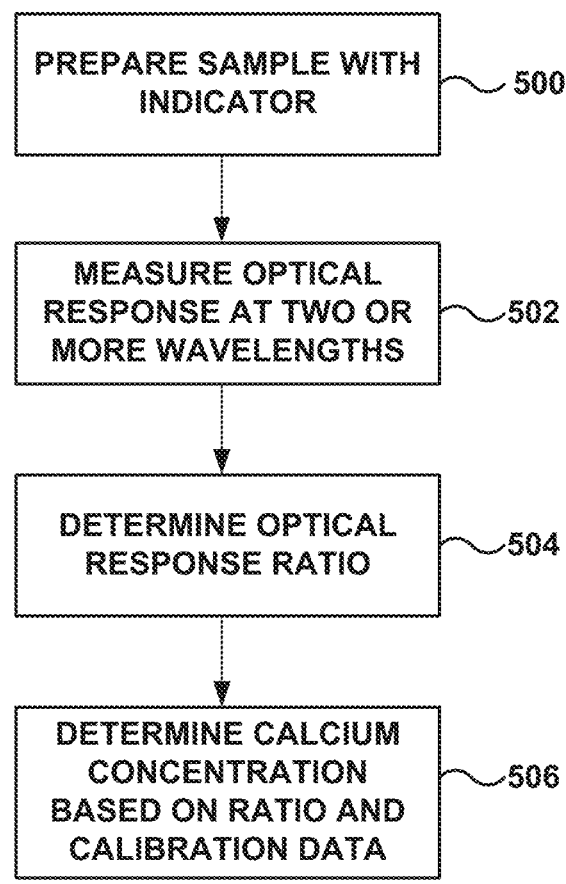
FIG. 5 is a flow diagram illustrating an example technique for measuring the concentration of calcium in an aqueous sample using an optical sensor calibrated according to the technique of FIG. 4.

After calibrating optical sensor 100 to generate calibration curve data 142, the optical sensor may be used to measure the concentration of calcium in water samples having unknown calcium concentrations. FIG. 5 is a flow diagram illustrating an example technique for measuring the concentration of calcium in an aqueous sample using an optical sensor calibrated according to the disclosure.

With reference to FIG. 5, the example technique includes preparing an aqueous sample having an unknown concentration of calcium (500). For example, operating under the control of controller 136, optical sensor 100 may extract a sample of water from an industrial system (e.g., industrial water system 10) having an unknown concentration of calcium. Sample pump 150 may operate to draw the sample out of a flowing stream for mixing with one or more components to facilitate the optical analysis. For example, controller 136 may control indicator pump 152 and/or reagent pump 166 to add a target amount of indicator and/or one or more other reagents to the sample to facilitate subsequent optical analysis. In some implementations, the constituent components may pass through a mixer facilitate thorough mixing before being received by the sample receiving area 164 of optical sensor 100.

With the sample of water having the unknown concentration of calcium adequately prepared (e.g., with the addition of an indicator), optical emitter 160 can emit light into and optical detector 162 can detect light from the sample at multiple wavelengths, including at least the first wavelength and the second wavelength used to generate calibration curve data 142 (502). This can provide a first measured optical response corresponding to the first wavelength and a second measured optical response corresponding to the second wavelength for the sample having the unknown concentration of calcium. Controller 136 can generate an optical response ratio (e.g., by dividing the first measured optical response by the second measured optical response or vice versa) for the sample.

With reference to calibration curve data 142 stored in memory 140, controller 136 can relate the measured optical response ratio for the sample to a calcium concentration corresponding to that optical response ratio. When calibration curve data 142 relates a square root of calcium concentration to a measured optical response ratio, controller 136 may determine a measured calcium concentration for the sample having the unknown concentration of calcium with reference to memory 140 using the following equation:

$$[Ca]=(m^*x+b)^2 \quad \text{Equation 1:}$$

In Equation 1 above, [Ca] is the measured calcium concentration, x is the measured optical response ratio, m is a slope coefficient stored in memory, and b is the intercept coefficient stored in memory.

When calibration curve data 142 relates calcium concentration to a natural log of measured optical response ratio, controller 136 may determine a measured calcium concentration for the sample having the unknown concentration of calcium with reference to memory 140 using the following equation:

$$[Ca]=b+me^x \quad \text{Equation 2:}$$

In Equation 2 above, [Ca] is the measured calcium concentration, x is the measured optical response ratio, m is a slope coefficient stored in memory, and b is based on the intercept coefficient stored in memory.

In some examples, controller 136 can take various control actions based on the calcium concentration measured in the sample. For example, controller 136 may compare the measured calcium concentration against one or more thresholds stored in memory 140 and take a corresponding control action if the measured concentration exceeds the threshold. In the example implementation of FIG. 1, controller may control the system to adjust the temperature and/or flow rate and/or make-up of the cooling water. Additionally or alternatively, controller 136 may control pump 106 to control the introduction of one or more chemical agents into a cooling water stream based on the measured calcium concentration (e.g., start the pump, stop the pump, or adjust an operating rate of the pump).

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a non-transitory computer-readable storage medium, containing instructions. Instructions embedded or encoded in a computer-readable storage medium may cause a programmable processor, or other processor, to perform the method, e.g., when the instructions are executed. Non-transitory computer readable storage media may include volatile and/or non-volatile memory forms including, e.g., random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

The following examples may provide additional details about optical sensor systems and calibration techniques according to the disclosure.

EXAMPLES

A variety of calibration solutions were prepared for optical analysis. Each calibration solution was prepared using a reagent base having the following three components:

| Component | CAS Number | Function |
|---|---|---|
| Chlorophosphonazo-III | 1914-99-4 | Calcium Ion Complexing Dye |
| Citric Acid | 77-92-9 | pH Buffer |
| Sodium Citrate Tribasic Dihydrate | 6132-04-3 | Range Extender |

The reagent base was mixed with aqueous calcium standards in different relative proportions to provide multiple calibration solutions having result calcium concentrations ranging from 0 ppm to 1400 ppm calcium as calcium carbonate.

Figure 6A:
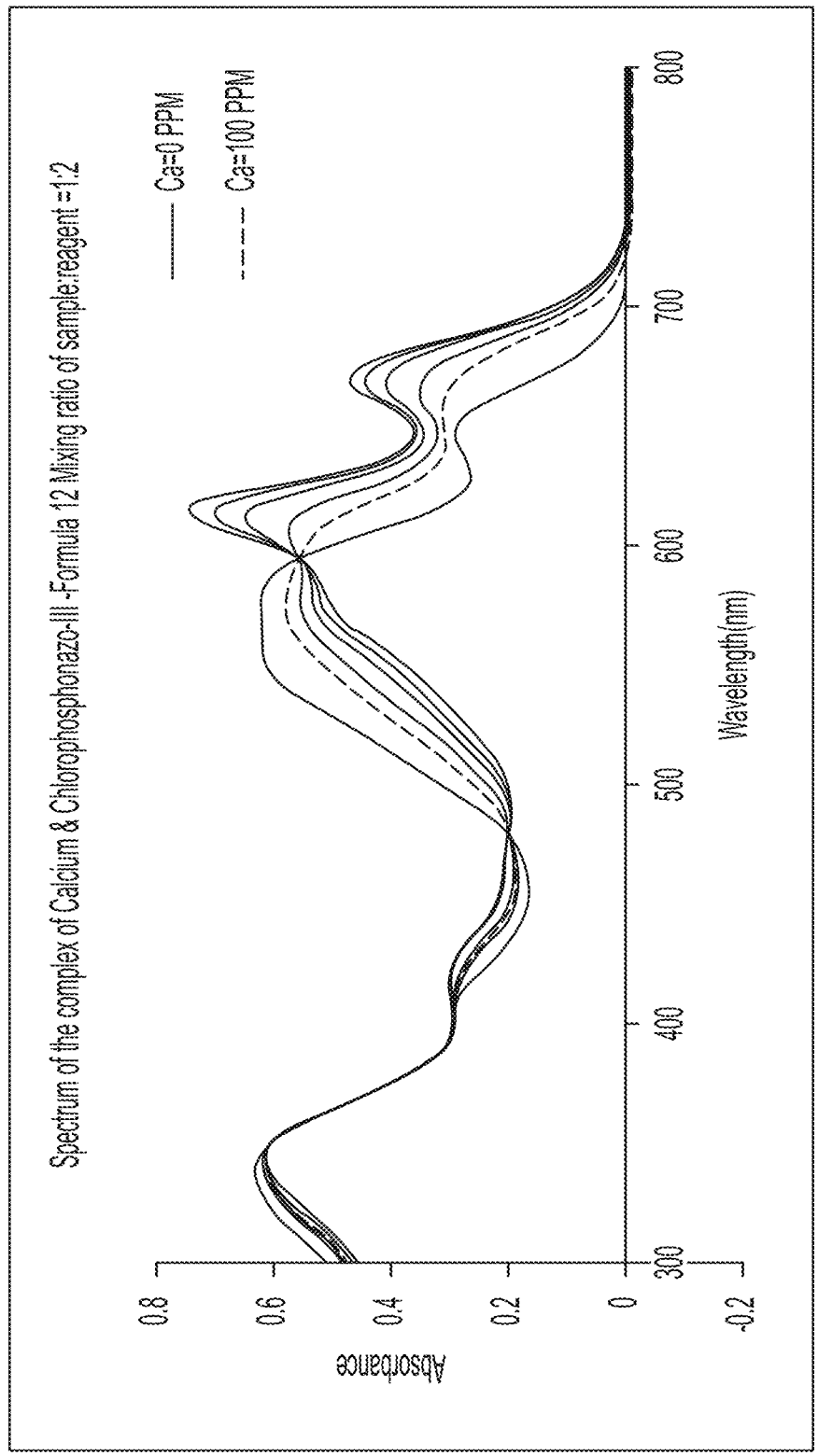
FIGS. 6A and 6B are plots of the absorbance data for multiple samples having different calcium concentrations over a range of wavelengths.
Figure 6B:
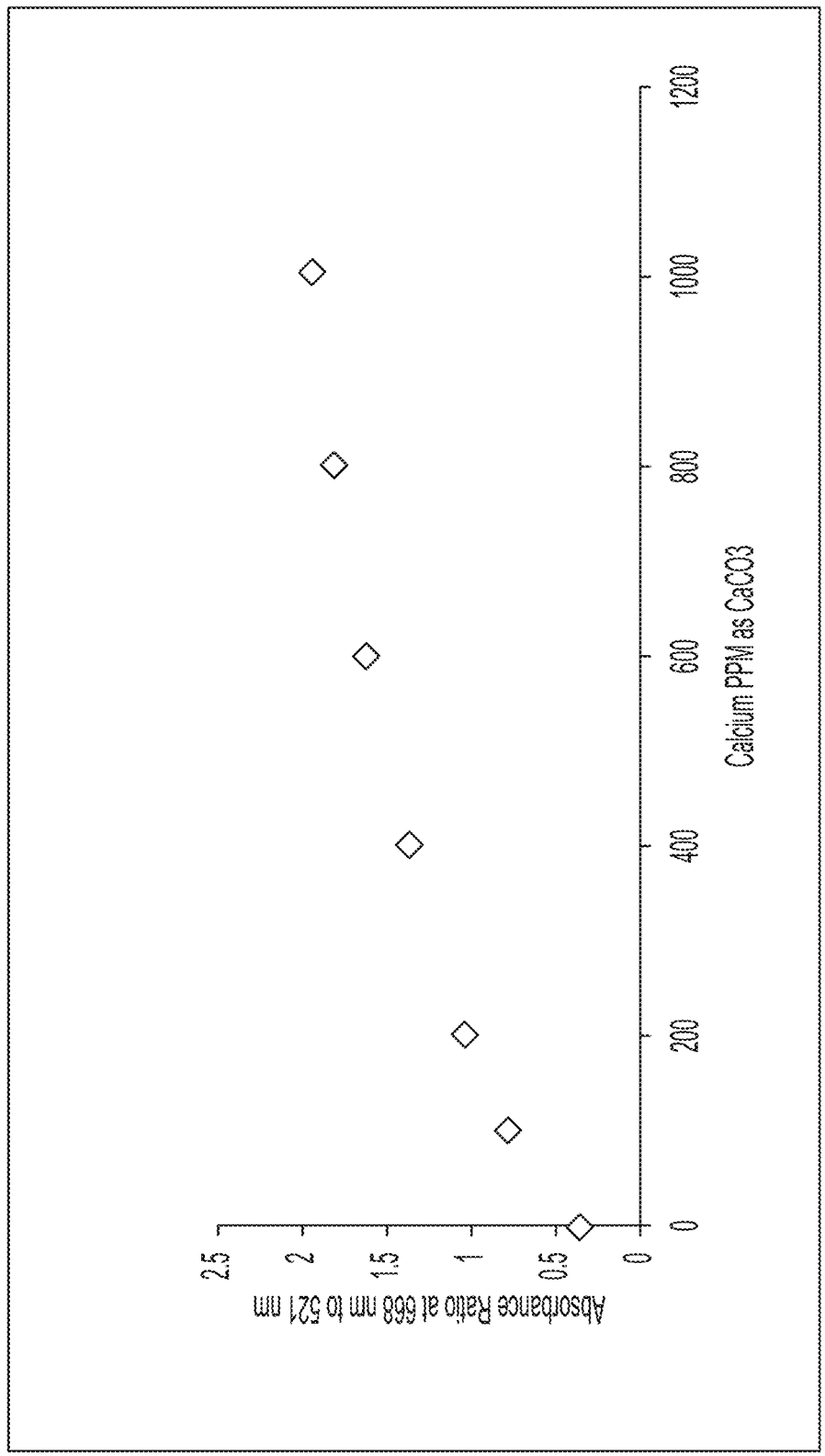

The different calibration solutions were optically analyzed using a spectrometer to obtain absorbance measurements for the samples over wavelengths ranging from 300 nm to 800 nm. FIGS. 6A and 6B are plots of the absorbance data for multiple mixtures having different calcium concentrations over a range of wavelengths. Based on the data and the amount of absorbance separation between the mixtures at a given wavelength, a first wavelength of 668 nm and a second wavelength of 521 nm were selected for subsequent optical investigation.

Absorbance measurements of a specific calibration solution at the two selected wavelengths revealed that the relationship between absorbance and calcium concentration was decreasing with increasing calcium concentration at 521 nm but increasing with increasing calcium concentration at 668 nm. FIG. 3 discussed above illustrates the results of this analysis.

An absorbance ratio was calculated for the calibration solutions by dividing the absorbance of each sample at 668 nm by the absorbance for the sample at 521 nm. FIGS. 6A and 6B are plots of the absorbance ratios for each sample plotted on the y-axis relative to corresponding calcium concentration plotted on the x-axis.

Figure 7:
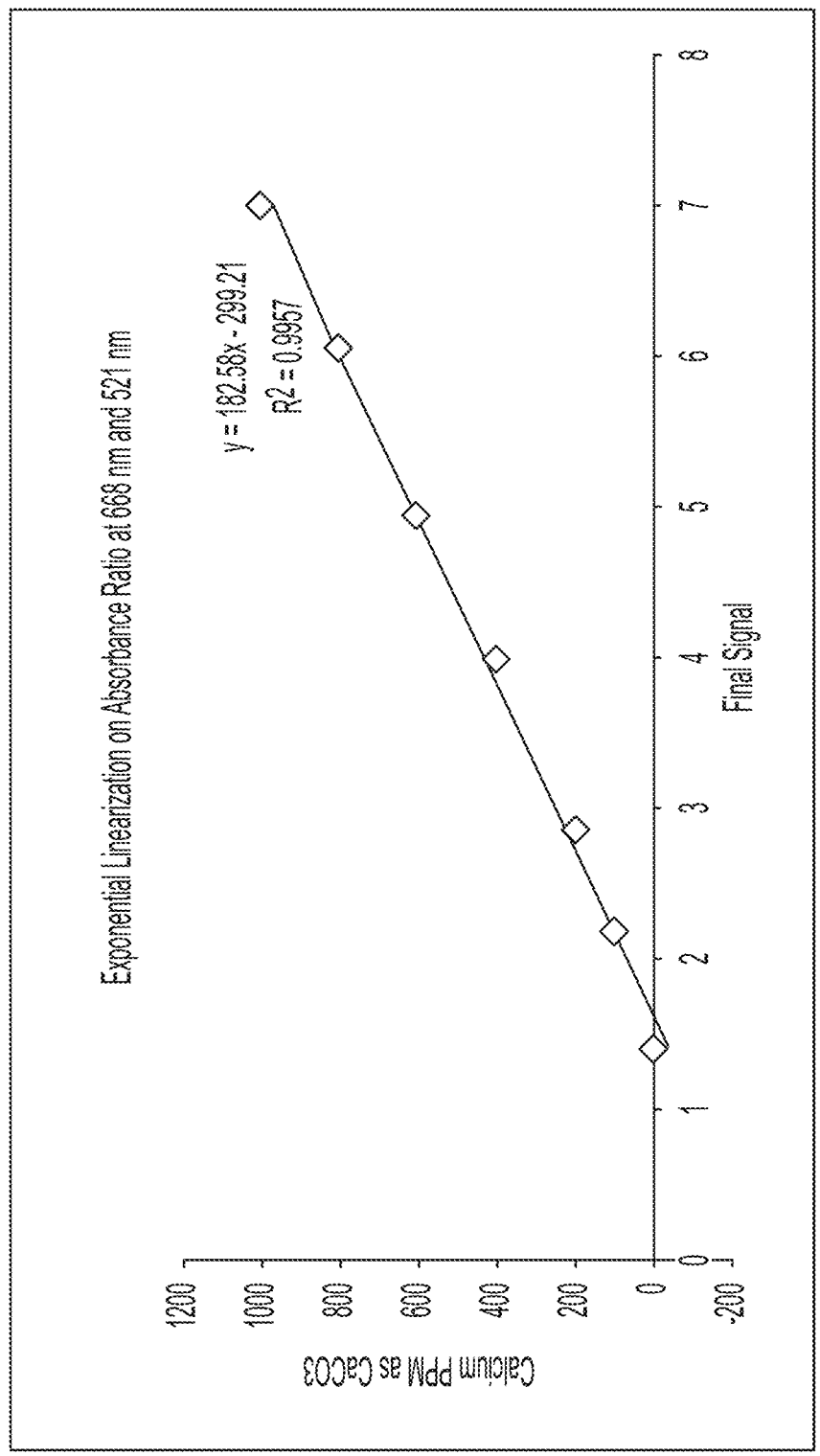
FIG. 7 is a plot of the calcium concentration plotted on the y-axis to the natural log of the absorbance ratio plotted on the x-axis for multiple experimental calibration solutions.

The absorbance ratio data illustrated in FIGS. 6A and 6B were linearized using exponential linearization by determining a calibration curve relating the calcium concentration (in parts per million) to the natural log of the optical response ratio for each calibration solution. FIG. 7 is a plot of the calcium concentration plotted on the y-axis to the natural log of the absorbance ratio plotted on the x-axis for each calibration solution. A linear calibration curve was fit to the data having the form y=mx+b, where the "m" coefficient was calculated as 182.6 and the "b" coefficient was calculated as 299.2, for the experimental data studied.

Figure 8:
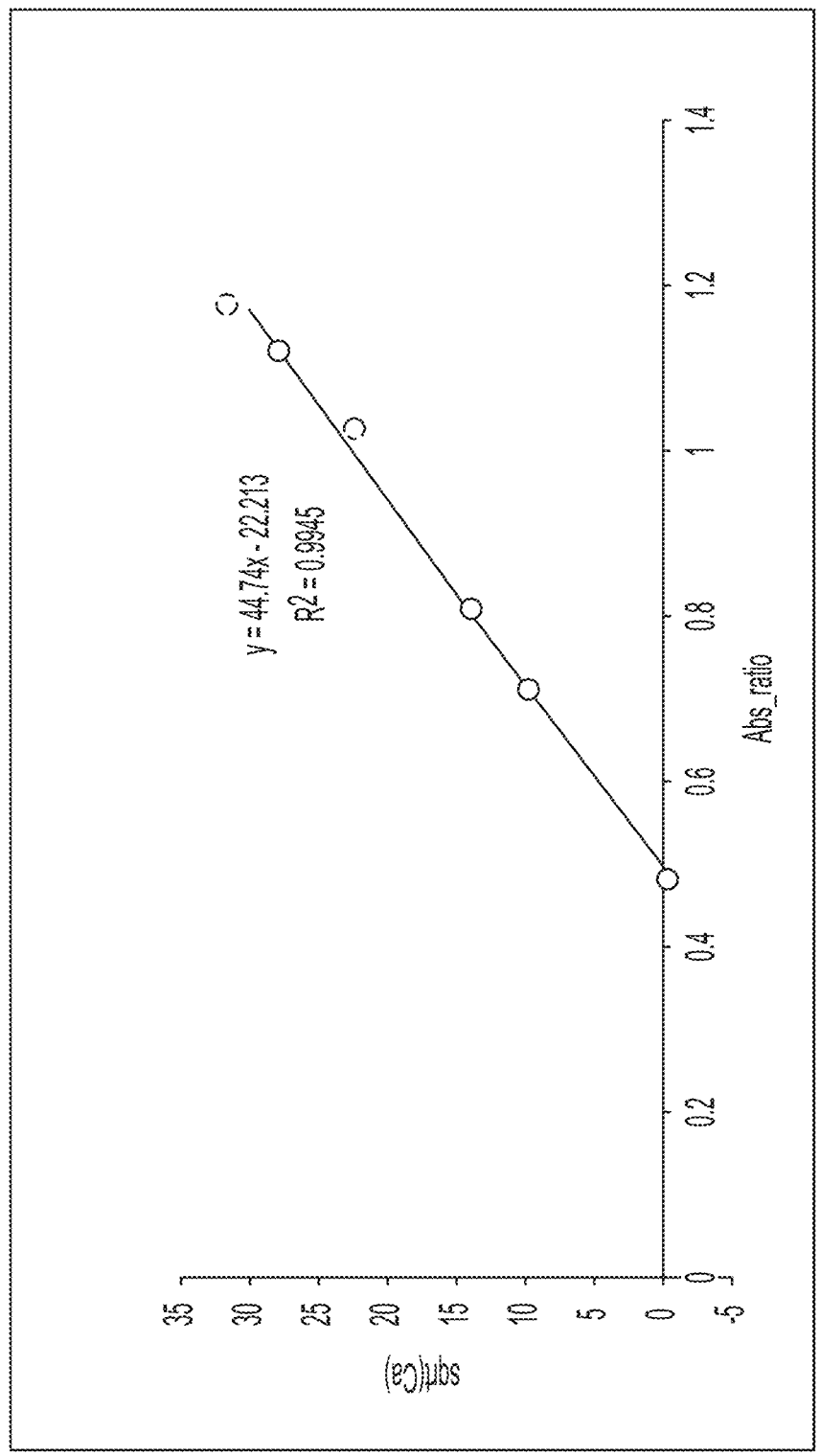
FIG. 8 is a plot of the square root of calcium concentration plotted on the y-axis to the absorbance ratio plotted on the x-axis for multiple experimental calibration solutions.

Separately, the absorbance ratio data illustrated in FIGS. 6A and 6B were linearized using a square root function by determining a calibration curve relating a square root of calcium concentration to optical response ratio for each calibration solution. FIG. 8 is a plot of the square root of calcium concentration plotted on the y-axis to the absorbance ratio plotted on the x-axis for each calibration solution. A linear calibration curve was fit to the data having the form y=mx+b, where the "m" coefficient was calculated as 44.7 and the "b" coefficient was calculated as 22.2, for the experimental data studied.

The invention claimed is:

1. A method of calibrating an optical sensor for measuring calcium, the method comprising:
    measuring, with an optical sensor, an optical response of a first calibration solution at a first wavelength to provide a first measured optical response for the first calibration solution and at a second wavelength to provide a second measured optical response for the first calibration solution, the first calibration solution comprising a first known concentration of calcium;
    measuring, with the optical sensor, the optical response of a second calibration solution at the first wavelength to provide a first measured optical response for the second calibration solution and at a second wavelength to provide a second measured optical response, the second calibration solution having a second known concentration of calcium;
    determining a first optical response ratio for the first calibration solution based on the first measured optical response for the first calibration solution and the second measured optical response for the first calibration solution;
    determining a second optical response ratio for the second calibration solution based on the first measured optical response for the second calibration solution and the second measured optical response for the second calibration solution;
    determining coefficients for a linear calibration curve relating an optical response measurement made by the optical sensor to a calcium concentration in a solution based on the first known concentration of calcium and first optical response ratio and the second known calcium concentration and the second optical response ratio, wherein the linear calibration curve is a first order equation having a form y=m*x+b, where m is a slope coefficient and x is the first optical response ratio divided by the second optical response ratio and (i) y is a square root of the calcium concentration and b is an intercept coefficient or (ii) y is a natural log of the calcium concentration and b is a natural log of the intercept coefficient, and
    storing the coefficients for the linear calibration curve in a memory associated with the optical sensor.

2. The method of claim 1, wherein y is the square root of the calcium concentration in the solution and b is the intercept coefficient.

3. The method of claim 1, wherein y is the natural log of the calcium concentration in the solution and b is the natural log of the intercept coefficient.

4. The method of claim 1, wherein
    determining the first optical response ratio comprises dividing the first measured optical response for the first calibration solution by the second measured optical response for the first calibration solution; and
    determining the second optical response ratio for the second calibration solution comprises dividing the first measured optical response for the second calibration solution by the second measured optical response for the second calibration solution.

5. The method of claim 1, wherein the first wavelength is within a range from 625 nm to 725 nm, and the second wavelength is within a range from 475 nm to 575 nm.

6. The method of claim 1, wherein the first wavelength is 668 nm and the second wavelength is 521 nm.

7. The method of claim 1, wherein at least one of the first wavelength and the second wavelength is a wavelength at an absorbance peak.

8. The method of claim 1, wherein the first known concentration of calcium and the second known concentration of calcium are each greater than 0.

9. The method of claim 1, wherein:
    the first known concentration of calcium is 0 ppm calcium; and
    the second known concentration of calcium is within a range from 10 ppm calcium to 2000 ppm calcium.

10. The method of claim 1, wherein the first calibration solution and the second calibration solution each comprise an indicator.

11. The method of claim 10, wherein the indicator is Chlorophosphonazo-III.

12. The method of claim 1, further comprising:
    automatically generating the first calibration solution by mixing a reagent comprising at least an indicator with a first calcium stock solution; and
    automatically generating the second calibration solution by mixing the reagent comprising at least an indicator with a second calcium stock solution.

13. The method of claim 1, wherein:
    a relationship between the optical response measurement made by the optical sensor and the calcium concentration in the solution is non-linear across a range of calcium concentrations;
    determining coefficients for the linear calibration curve comprises at least one of:
    (1) determining coefficients for a first order equation fitted to a line defined by a square root of the first known concentration of calcium and the first optical response ratio and a square root of the second known concentration of calcium and the second optical response ratio; and (2) determining coefficients for a first order equation fitted to a line defined by a natural log of the first known concentration of calcium and the first optical response ratio and a natural log of the second known concentration of calcium and the second optical response ratio.

14. The method of claim 1, further comprising:
extracting a sample of water containing an unknown concentration of calcium from an industrial water system;
mixing an indicator with the sample to form the solution,
measuring, with the optical sensor, the optical response of solution at the first wavelength and the second wavelength,
determining the calcium concentration in the solution based on the optical response of the solution measured at the first wavelength and the second wavelength and the stored coefficients for the linear calibration curve.

15. The method of claim 14, further comprising controlling addition of a calcium control agent into the industrial water system based on the determined calcium concentration.

16. The method of claim 1, wherein the optical response is absorbance.

17. A method of calibrating an optical sensor for measuring calcium, the method comprising:
measuring, with an optical sensor, an optical response of a first calibration solution at a first wavelength that is 668 nm to provide a first measured optical response for the first calibration solution and at a second wavelength that is 521 nm to provide a second measured optical response for the first calibration solution, the first calibration solution comprising a first known concentration of calcium;
measuring, with the optical sensor, the optical response of a second calibration solution at the first wavelength to provide a first measured optical response for the second calibration solution and at a second wavelength to provide a second measured optical response, the second calibration solution having a second known concentration of calcium;
determining a first optical response ratio for the first calibration solution based on the first measured optical response for the first calibration solution and the second measured optical response for the first calibration solution;
determining a second optical response ratio for the second calibration solution based on the first measured optical response for the second calibration solution and the second measured optical response for the second calibration solution;
determining coefficients for a linear calibration curve relating an optical response measurement made by the optical sensor to a calcium concentration in a solution based on the first known concentration of calcium and first optical response ratio and the second known calcium concentration and the second optical response ratio; and
storing the coefficients for the linear calibration curve in a memory associated with the optical sensor.

18. A method of calibrating an optical sensor for measuring calcium, the method comprising:
automatically generating a first calibration solution by mixing a reagent comprising at least an indicator with a first calcium stock solution;
automatically generating a second calibration solution by mixing the reagent comprising at least an indicator with a second calcium stock solution;
measuring, with an optical sensor, an optical response of the first calibration solution at a first wavelength to provide a first measured optical response for the first calibration solution and at a second wavelength to provide a second measured optical response for the first calibration solution, the first calibration solution comprising a first known concentration of calcium;
measuring, with the optical sensor, the optical response of the second calibration solution at the first wavelength to provide a first measured optical response for the second calibration solution and at a second wavelength to provide a second measured optical response, the second calibration solution having a second known concentration of calcium;
determining a first optical response ratio for the first calibration solution based on the first measured optical response for the first calibration solution and the second measured optical response for the first calibration solution;
determining a second optical response ratio for the second calibration solution based on the first measured optical response for the second calibration solution and the second measured optical response for the second calibration solution;
determining coefficients for a linear calibration curve relating an optical response measurement made by the optical sensor to a calcium concentration in a solution based on the first known concentration of calcium and first optical response ratio and the second known calcium concentration and the second optical response ratio; and
storing the coefficients for the linear calibration curve in a memory associated with the optical sensor.

19. A method comprising:
measuring, with an optical sensor, an optical response of a first calibration solution at a first wavelength to provide a first measured optical response for the first calibration solution and at a second wavelength to provide a second measured optical response for the first calibration solution, the first calibration solution comprising a first known concentration of calcium;
measuring, with the optical sensor, the optical response of a second calibration solution at the first wavelength to provide a first measured optical response for the second calibration solution and at a second wavelength to provide a second measured optical response, the second calibration solution having a second known concentration of calcium;
determining a first optical response ratio for the first calibration solution based on the first measured optical response for the first calibration solution and the second measured optical response for the first calibration solution;
determining a second optical response ratio for the second calibration solution based on the first measured optical response for the second calibration solution and the second measured optical response for the second calibration solution;
determining coefficients for a linear calibration curve relating an optical response measurement made by the optical sensor to a calcium concentration in a solution based on the first known concentration of calcium and first optical response ratio and the second known calcium concentration and the second optical response ratio;
storing the coefficients for the linear calibration curve in a memory associated with the optical sensor;

extracting a sample of water containing an unknown concentration of calcium from an industrial water system;

mixing an indicator with the sample to form the solution;

measuring, with the optical sensor, the optical response of solution at the first wavelength and the second wavelength; and determining the calcium concentration in the solution based on the optical response of the solution measured at the first wavelength and the second wavelength and the stored coefficients for the linear calibration curve.

20. The method of claim 19, further comprising controlling addition of a calcium control agent into the industrial water system based on the determined calcium concentration.

21. The method of claim 19, wherein the linear calibration curve is a first order equation having a form $y=m*x+b$, where y is a square root of the calcium concentration in the solution, x is the first optical response ratio divided by the second optical response ratio, m is a slope coefficient, and b is an intercept coefficient.

22. The method of claim 19, wherein the linear calibration curve is a first order equation having a form $y=m*x+b$, where y is a natural log of the calcium concentration in the solution, x is the first optical response ratio divided by the second optical response ratio, m is a slope coefficient, and b is a natural log of an intercept coefficient.

* * * * *